US011788106B2

(12) United States Patent
Johnson et al.

(10) Patent No.: US 11,788,106 B2
(45) Date of Patent: *Oct. 17, 2023

(54) REDUCING INSOLUBLE DEPOSIT FORMATION IN ETHANOL PRODUCTION

(71) Applicant: Kurita America, Inc., St. Michael, MN (US)

(72) Inventors: Roy Johnson, Oconomowoc, WI (US); Paul Young, Wheaton, IL (US)

(73) Assignee: Kurita America, Inc., St. Michael, MN (US)

(*) Notice: Subject to any disclaimer, the term of this patent is extended or adjusted under 35 U.S.C. 154(b) by 12 days.

This patent is subject to a terminal disclaimer.

(21) Appl. No.: 17/208,696

(22) Filed: Mar. 22, 2021

(65) Prior Publication Data
US 2021/0363555 A1 Nov. 25, 2021

Related U.S. Application Data

(63) Continuation of application No. 16/178,107, filed on Nov. 1, 2018, now Pat. No. 10,954,535, which is a continuation of application No. 15/296,856, filed on Oct. 18, 2016, now abandoned, which is a continuation of application No. 14/515,838, filed on Oct. 16, 2014, now abandoned, which is a continuation of application No. 14/093,989, filed on Dec. 2, 2013, now abandoned, which is a continuation of application No. 13/489,067, filed on Jun. 5, 2012, now Pat. No. 8,609,399, which is a continuation of application No. 13/274,075, filed on Oct. 14, 2011, now Pat. No. 8,415,137, which is a continuation of application No. 11/873,630, filed on Oct. 17, 2007, now Pat. No. 8,039,244.

(51) Int. Cl.
*C12P 9/00* (2006.01)
*C12P 7/06* (2006.01)

(52) U.S. Cl.
CPC ............ *C12P 9/00* (2013.01); *C12P 7/06* (2013.01); *Y02E 50/10* (2013.01)

(58) Field of Classification Search
CPC ............ Y02E 50/10; C12P 9/00; C12P 7/06
See application file for complete search history.

(56) References Cited

U.S. PATENT DOCUMENTS

| | | | |
|---|---|---|---|
| 2,515,157 | A | 7/1950 | Parsons |
| 4,914,029 | A | 4/1990 | Caransa et al. |
| 5,756,714 | A | 5/1998 | Antrim et al. |
| 6,156,563 | A | 12/2000 | Kampen |
| 6,660,506 | B2 | 12/2003 | Nguyen |
| 7,048,803 | B2 | 5/2006 | Williams |
| 7,244,597 | B2 | 7/2007 | Veit et al. |
| 8,039,244 | B2 | 10/2011 | Johnson et al. |
| 2002/0006647 | A1 | 1/2002 | Veit et al. |
| 2002/0187528 | A1 | 12/2002 | Veit et al. |
| 2005/0026261 | A1 | 2/2005 | Otto et al. |
| 2005/0272137 | A1 | 12/2005 | Veit et al. |
| 2007/0155001 | A1 | 7/2007 | Veit et al. |

FOREIGN PATENT DOCUMENTS

WO WO 2008/036916 3/2008

OTHER PUBLICATIONS

Brandes et al., Marine Chemistry, 2007, available online Nov. 2006, vol. 103, p. 250-265. (Year: 2006).*
"Genencor Introduces a Greener, More Efficient Enzyme for Ethanol Production—New Maxaliq™ ONE product improves process efficiency in production of biofuels from corn," Jun. 20, 2007, *Genencor®, News for Immediate Release.*
Amjad et al., "The Influence of Recirculating Water Impmities on the Performance of Calcium Phosphate Inhibiting Polymers," *Corrosion 99*, NACE International, Paper No. 118, 1999.
Applegate et al., "Phytase: Basics of Enzyme Function"May 2004, *Farm Animal Management@Purdue.* AS-560-W:1-5.
Belyea et al., "Element Concentrations of Dry-Grind Com-Processing Streams" 2006, *Applied Biochemistry and Biotechnology*, 134:113-128.
Cromwell, G.L., *Proc. Distiller Feed. Red. Conf.* (1979) 40-52.
Huang et al., *Chemosphere* (2002) 49: 413-420.
Koniczny-Janda et al., "The Application of Phytase in Ethanol Production from Grain", 52$^{nd}$ *Starch Convention*, Detmold, Germany, 2001, pp. 1-15 (abstract and paper).
Kwiatkowski et al., "Modeling the process and costs of fuel ethanol production by the corn dry-grind process," Industrial Crops and Products 23 (2006) 288-296.
Lantero et al., "The Role of Pretreatment in Granular Starch Substrate(s) for Ethanol Production," Genencor International, Fuel Ethanol Workshop & Expo, Jun. 21, 2006, Milwaukee, WI.
Lei et al., *Biotechnology Letters* (2003) 25: 1787-1794.
May, R., *Analytical Chemistry* (1959) 31 (2): 308-310.
McCance et al., CCCXX. Phytin in Human Nutrition (1935): 2694-2699.
Parsons, G, "Treatment of Corn Steepwater", Jul. 1950 (U.S. Pat. No. 2,515,157).
Rausch et al., *Applied Biochemistry and Biotechnology* (2006) 128: 47-86.
Shetty et al., "New Liquefaction Enzyme System for Fuel Ethanol", *International Fuel Ethanol Workshop & Exposition*, St. Louis, Missouri, 2007, pp. 1-27.

(Continued)

*Primary Examiner* — Kade Ariani
(74) *Attorney, Agent, or Firm* — MERCHANT & GOULD P.C.

(57) ABSTRACT

The present inventors have surprisingly discovered that phytic acid tenaciously precipitates with soluble metals in food or fuel ethanol-processing fluid, producing insoluble organometallic salt deposit or scale on the processing equipment that must be removed in order to facilitate further ethanol processing. The present invention relates to converting phytic acid salts or phytates to inorganic phosphates to improve metal solubility and reduce deposition within processing equipment.

17 Claims, No Drawings

(56) References Cited

OTHER PUBLICATIONS

Shetty et al., "Phytase in Fuel Ethanol Production Offers Economical and Environmental Benefits", *110 Int'l Sugar J.*, vol. 160, 2008, pp. 160-174.
Sullivan et al., "A Multifunctional Additive for Deposit Control," *Corrosion 96*, The NACE International Annual Conference and Exposition, Paper No. 158, 1996.
Wilkins et al., "Analysis of heat transfer fouling by thin stillage from dry grind corn processing facilities", *Ph.D. Dissertation, University of Illinois*, Urbana-Champaign, 2004, pp. 1-110.
Third Party IDS Submission in U.S. Appl. No. 13/489,067 dated Dec. 13, 2012.
Third Party IDS Submission in U.S. Appl. No. 13/489,067 dated Jan. 18, 2013.

* cited by examiner

REDUCING INSOLUBLE DEPOSIT FORMATION IN ETHANOL PRODUCTION

This application is a continuation of U.S. application Ser. No. 16/178,107, filed Oct. 31, 2018, now U.S. Pat. No. 10,954,535, issued Mar. 23, 2021, which is a continuation of U.S. application Ser. No. 15/296,856, filed Oct. 18, 2016, which is a continuation of U.S. application Ser. No. 14/515, 838, filed Oct. 16, 2014, which is a continuation of U.S. application Ser. No. 14/093,989, filed Dec. 2, 2013, which is a continuation of U.S. application Ser. No. 13/489,067, filed Jun. 5, 2012, now U.S. Pat. No. 8,609,399, issued Dec. 17, 2013, which is a continuation of U.S. application Ser. No. 13/274,075, filed Oct. 14, 2011, now U.S. Pat. No. 8,415, 137, issued Apr. 9, 2013, which is a continuation of U.S. application Ser. No. 11/873,630, filed Oct. 17, 2007, now U.S. Pat. No. 8,039,244, issued Oct. 18, 2011 and which applications are incorporated herein by reference. A claim of priority, to the extent appropriate, is made.

FIELD OF THE INVENTION

The present inventors have surprisingly discovered that the phytic acid tenaciously precipitates with soluble metals in food or fuel ethanol-processing fluid, producing insoluble organometallic salt deposit or scale on the processing equipment that must be removed in order to facilitate further ethanol processing. The present invention relates to converting phytic acid salts or phytates to inorganic phosphates to improve metal solubility and reduce deposition within processing equipment.

BACKGROUND

Fermentation of sugars and polysaccharides into alcohol is a rapidly developing technology for producing liquid fuel, such as gasohol or E85, which are the most common examples in the United States and contain varying amounts of ethanol and gasoline. Billions of gallons of fuel ethanol are produced every year through the fermentation of grains, plants and feedstock, primarily corn. Other types of feedstock such as sugar care and cellulose are also increasing in importance.

Ethanol producers have found scale deposits on processing equipment at several stages of ethanol processing. These scale deposits are known to impede heat transfer and flow, and interfere with the proper operation of mechanical devices used in ethanol processing. The deposits tend to be most severe or tenacious on hot surfaces, and where the pH of the processing liquid is highest (about 4.5), but deposits may also form at lower pH values and on cooler surfaces. There remains a need for methods and compositions for reducing this scale formation.

SUMMARY

The present inventors have unexpectedly discovered that phytic acid tenaciously precipitates with soluble metals in food or fuel ethanol-processing fluid, producing insoluble organometallic salt deposit or scale on the processing equipment that must be removed in order to facilitate further ethanol processing. The present invention relates to converting phytic acid salts or phytates to inorganic phosphates to improve metal solubility and reduce deposition within processing equipment.

In an embodiment, the present method can reduce insoluble deposit formation in equipment that contacts food or fuel ethanol-processing fluids. The method can include: adding an agent to the ethanol-processing fluids after fermentation; converting the insoluble material to a soluble residue by action of the agent; and removing the soluble residue from the equipment that contacts the ethanol-processing fluids. The method can also include identifying the insoluble deposit from the ethanol-processing fluids.

In an embodiment, the present method includes adding an enzyme with phytase activity to the ethanol-processing fluids after fermentation; converting the phytate to orthophosphate by action of the enzyme; and removing the soluble orthophosphate from the equipment that contacts the ethanol-processing fluids. This embodiment can also include identifying the insoluble deposit from the ethanol-processing fluids as phytic acid or a salt of phytic acid.

DETAILED DESCRIPTION

Definitions

As used herein, the term "mash" refers to a mixture or slurry of milled grain, process water and an enzyme such as alpha amylase, after the mixture has been subjected to a high temperature pressure "cook" and introduced into fermentation tank during ethanol processing.

"Cook water" refers to process water generated and/or used during cook process, where the starch content of milled grain is physically and chemically prepared for fermentation, typically by application of heat and by the action of enzymes such as amylase.

"Liquefaction" or "liquefy" means a process by which starch is converted to shorter chain and less viscous dextrins. Generally, this process involves gelatinization of starch simultaneously with or followed by the addition of enzymes such as amylase.

The term "liquefaction slurry" refers to combination of hot slurry, and the slurries from primary and secondary liquefaction produced during ethanol processing.

Hot slurry is formed when milled grain is first mixed with process water and the formed slurry is treated with an enzyme such as a-amylase and then heated to temperatures of up to 190° F. to reduce the viscosity of the slurry. The slurry is then pumped through a pressurized jet cooker for flash condensation during primary liquefaction. After flash condensation and cooling, the primary liquefaction slurry is held at high temperature for one to two hours to provide enough time for the amylase to fully break down the starch into short chain dextrins. During secondary liquefaction or "saccharification", a second enzyme (such as glucoamylase) is added, and the formed slurry is moved into fermentation tanks. Liquefaction and saccharification may take place successively or simultaneously.

"Fermentation" refers to a process by which the sugars in the slurry or mash from liquefaction/saccharification are converted into alcohol by the action of yeast in the fermentation tanks or fermentors. The mash is allowed to ferment for 50-60 hours, resulting in a mixture that contains about 15% ethanol as well as the solids from the grain and added yeast, i.e. the "fermentation slurry." Once fermentation is complete, the mash or slurry is called "beer" and is moved into beer wells to be used for ethanol distillation and recovery.

The term "whole stillage" refers to the mash or solids remaining after ethanol is removed from beer or beer mash using a stripper column. The term is used interchangeably with the term "thick stillage." Whole stillage is typically 11% to 14% solids and contains all of the other non-starch components of the grains that pass through the process (germ, protein, gluten, hull & fiber etc.).

"Thin stillage" refers to the liquid removed from the mash in ethanol production. Thin stillage is about 5% dry matter and about 95% water. Thin stillage can be reintroduced into the cooking and distillation processes to extract additional ethanol. Thin stillage that is recycled to the beginning of the dry-grind process is known as "backset" and is used to conserve water used in processing.

The term "beerstone" refers to a hard organometallic scale deposited on fermentation equipment and that is primarily calcium oxalate. Although beerstone is a commonly formed deposit during ethanol processing, not all solid deposits formed are beerstone.

The term "phytase unit" refers to the amount of phytase enzyme that can liberate one micromole of ortho-phosphate from insoluble phytate in one minute, assuming optimal conditions of temperature and pH.

Methods of the Invention

The commercial processing of ethanol produces aqueous slurries of plant grains and fibers that release phytic acid. The present inventors have unexpectedly discovered that the phytic acid tenaciously precipitates with soluble metals in the processing fluid, producing insoluble organometallic salt deposit or scale on the processing equipment that must be removed in order to facilitate further ethanol processing. The present invention relates to converting insoluble phytic acid salts (i.e., phytate) to soluble inorganic phosphates and an organic compound (i.e., inositol), which can improve metal solubility and reduce deposition within processing equipment.

The present invention provides a method for reducing or even preventing the formation of insoluble material, deposits, or scale on equipment used in processing of food or fuel ethanol. According to the method, the deposit or the material forming the deposit can be converted into a soluble material by the action of an agent capable of degrading or breaking down the insoluble deposit or material that forms the deposit. The soluble material can then be easily removed from the equipment or processing system, by standard methods or conventional means known to those of skill in the art.

The method can include identifying content of the deposit.

In an embodiment, the method of the present invention includes reducing the formation of insoluble deposits during ethanol processing. During commercial food and fuel ethanol processing, the aqueous slurries of plant grains and fibers produce acidic residues that interact with soluble metals in ethanol-processing fluids to produce organometallic precipitates. Many of these precipitates are insoluble solids that deposit as scale on processing equipment and interfere with downstream processing of ethanol, by impairing heat transfer and causing production interruptions. In an aspect, the solid deposit formed in this manner is beerstone, composed primarily of calcium oxalate. In another aspect, the aqueous slurries of plant grains and fibers form phosphate salts with dissolved metals present in ethanol processing fluid, such as salts of magnesium or calcium phosphate, for example. Various types of phosphate salts can be formed during ethanol processing including, without limitation, newberyite, bobierite, struvite (Mg salts), brushite, fluorapatite, hydroxyapatite (Ca salts), etc. In an aspect, the phosphate salt is a salt of a dissolved metal and phytic acid ($C_6H_{18}O_{24}P_6$; myoinositol hexakisphosphate, a phosphate ester of inositol) that is released by the plant grains and fibers present in the aqueous slurries. In another aspect, the phosphate salt is magnesium phytate. Phytate salts have been shown to form tenacious or insoluble precipitates in the presence of polar protic solvents such as water and ethanol, both of which are present in various concentrations during ethanol processing. Therefore, in an aspect, the method of the present invention provides for reducing or removing phytate that can deposit on ethanol processing equipment.

In an embodiment, the method of the present invention includes identifying the insoluble material formed during ethanol processing. Many different organometallic salts may be formed by the plant grains and fibers present in ethanol processing fluids. The solubility products of each salt may vary with processing conditions such as temperature and pH. Accordingly, the method can include chemically and/or geologically identifying the deposit or materials susceptible to deposit, which can aid in reducing or removing the insoluble deposit from the processing equipment and processing fluids. The insoluble material may be identified by standard methods known to those of skill in the art, including dry analysis methods such as x-ray fluorescence (XRF) or oxidation, followed by elemental analysis, for example, or wet analysis methods such as acid-base neutralization reactions, for example. In an aspect, the insoluble material is identified as a phosphate salt. In another aspect, the insoluble material is identified as a phytate salt, and in yet another aspect, the insoluble deposit is identified as magnesium phytate.

A considerable amount of the phosphorus or phosphate content in plant grains and fibers is in the form of phytic acid (as identified by standard analysis methods such as high temperature sample oxidation to ash), and commercial processing of these plant grains and fibers leads to release of phytic acid. These phytic acid concentrations in liquids, such as ethanol-processing fluids, can be high enough to cause precipitation of metal phytate salts, such as magnesium phytate, and subsequent deposit formation, in ethanol processing equipment. The formed phytates can impair heat transfer and cause production interruptions. A small amount of phytic acid is naturally broken down into soluble byproducts (i.e., soluble phosphates) during fermentation, but a large quantity (i.e., approximately 30-35%) of the phosphorus or phosphate in the stillage and syrup remains as phytic acid or phytate.

Metal phytate salts are generally much less soluble than the corresponding metal phosphates. For example, magnesium phytate is more than an order of magnitude less soluble than magnesium phosphate, and therefore, tends to precipitate out more readily than the more soluble magnesium phosphate. One way of causing phytate to precipitate is to heat a stable solution of magnesium phytate. Because phytate is less soluble at higher temperatures, a temperature is eventually reached where precipitation occurs, and this temperature is lower than the temperature at which magnesium phosphate would precipitate out. The temperature at which precipitation occurs is a function of pH and concentration of magnesium and phosphate or phytate ions. Assuming similar pH conditions, a solution of magnesium phosphate must be heated to about 40° C. more than a magnesium phytate solution, in order for the phosphate salt to precipitate out, even where the concentration of magnesium and phosphate ions were far greater than the concentration of magnesium and phytate ions, as shown in Table 1:

TABLE 1

Solubility of Magnesium with Phosphate and Phytate

| Solution | pH | Temp (° C.) | Precipitate(+/−) |
|---|---|---|---|
| 2100 ppm $Mg^{2+}$ | 5.2 | 40 | − |
| 8400 ppm $PO_4^{3-}$ | 5.2 | 60 | − |
| (as phosphate) | 5.2 | 90 | + |
|  | 5.76 | 60 | − |
|  | 5.76 | 80 | ++ |
| 800 ppm $Mg^{2+}$ | 4.23 | 80 | − |
| 3600 ppm $PO_4^{3-}$ | 4.52 | 60 | − |
| (as phytate) | 4.52 | 80 | + |
|  | 4.97 | 40 | − |
|  | 4.97 | 60 | ++ |
|  | 5.36 | 21 | − |
|  | 5.36 | 40 | ++ |
|  | 5.6 | 21 | + |

Furthermore, the presence of ethanol also reduces the solubility of magnesium phytate. Table 2 indicates that precipitation of the phytate salt occurred at much lower temperature in the presence of ethanol, even at very similar pH. In the table, the water and ethanol columns indicate the temperature at which a precipitate became visible in a solution containing 800 ppm $Mg^{2+}$ and 3600 ppm phytic acid.

TABLE 2

Solubility in Presence of Ethanol

| pH | Temperature (° C.; in 100% water solution) | Temperature (° C.; in 13% ethanol/87% water solution) |
|---|---|---|
| 4.35 |  | 40 |
| 4.52 | 80 |  |
| 4.53 |  | 30 |
| 4.6 |  | 21 |
| 4.97 | 60 |  |
| 5.36 | 40 |  |
| 5.6 | 21 |  |

In an embodiment, the present invention provides a method for reducing or removing insoluble material, such as phytate precipitates, by the action of an agent added to ethanol processing fluids. In an aspect, the agent is an acidic compound that can break down organic phosphates and phosphonates into soluble inorganic phosphates in the presence of a strong oxidizer or oxidizing agent. For example, a persulfate can degrade the insoluble phytate through acid digestion. In another aspect, the agent is an acidic compound that, in combination with ultraviolet light, can break down organic phosphates and phosphonates into soluble inorganic phosphates. In an embodiment, the agent is an enzyme capable of digesting or degrading (e.g., hydrolyzing) organic phosphates or phosphonates into soluble inorganic phosphates and an organic compound. For example, the agent can be a phytase, which can hydrolyze phytate to inorganic phosphate and inositol.

Phytase is an enzyme known to be capable of breaking down the phytic acid found in plant material. It is currently used primarily in animal feed applications, where it helps convert insoluble organic phosphates into soluble phosphorus that is more readily available to the animal's digestive system, and thereby also reduces environmental contamination by insoluble phosphate salts such as phytates. In ethanol processing, the phytase has been used to increase the bioavailability of phosphorus for the action of yeast in pre-saccharification and fermentation. Similarly, phytase has also been used in the liquefaction stage, or prior to fermentation to improve the activity of α-amylase.

Phytase is commercially available and can be derived from a variety of sources. In an aspect, the phytase is obtained from plants or microorganisms, such as bacteria, or from fungi, such as yeast or filamentous fungi, as disclosed in U.S. Patent Pub. No. 20050272137, for example, and incorporated herein by reference. Plant phytases may be derived from wheat-bran, maize, soybean, or lily pollen. Bacterial phytases may be derived from various bacterial sources including, without limitation, *Bacillus, Pseudomonas,* or *Escherichia,* preferably *B. subtilis* or *E. coli.* In another aspect, the phytase is a yeast phytase derived from *Saccharomyces* or *Schwanniomyces,* preferably *Saccharomyces cerevisiae* or *Schwanniomyces occidentalis.* In yet another aspect, phytases may be derived from filamentous fungi, including, but not limited to, species from the genus *Aspergillus, Thermomyces, Myceliophthora, Manascus, Penicillium, Peniophora, Agrocybe,* and the like.

Suitable commercially available phytases include, without limitation, those sold under the tradenames MAX-ALIQ™ ONE, by Genencor (Beloit, Wis.), RONOZYME® P5000 by Novozymes (Denmark), PHYTASE 5000L by DSM Food Specialties (France), NATUPHOS® 5000 by BASF (Germany), and PHYZYME™ XP 10000 by Danisco Animal Nutrition (St. Louis, Mo.). Suitable commercially available phytase enzyme may also be obtained from suppliers including, without limitation, Deerland Enzymes (Kennesaw, Ga.).

In an embodiment, phytase is added to ethanol processing equipment and/or processing fluid at a time point and under conditions required for the particular type of equipment or stage of ethanol processing. In an aspect, phytase is added to fermentation fluid to reduce formation of insoluble deposits in downstream ethanol processing equipment. In another aspect, phytase is added to ethanol processing fluids downstream of the fermentation process, such as, for example, beer, whole stillage, thin stillage, backset, centrate, or a mixture of these fluids. In an embodiment, phytase is added to thin stillage or backset. In an aspect, phytase is added to thin stillage or backset in line, i.e. the enzyme is introduced directly into thin stillage or backset-containing equipment during ethanol processing. In another aspect, phytase is added to thin stillage or backset offline, i.e. the enzyme is added to thin stillage or backset contained in a separate vessel or tank. Phytase-treated thin stillage or backset can then be cycled back into processing lines from the vessel or tank.

In an embodiment, the present invention provides a method in which the agent or enzyme is introduced into the ethanol-processing fluid under optimal conditions of temperature and pressure. Where the agent is phytase, the term "optimal conditions" refers to those conditions of concentration, temperature, residence time or reaction time, and pH that allow sufficient reaction with soluble phytate, phytate suspension, phytate precipitate, or insoluble phytate scale that reduces the level of the phytase deposit to an amount acceptable for operation of the ethanol plant or process. In an embodiment, the conditions provide for complete hydrolysis of soluble phytate and phytate suspension.

In an aspect, the phytase is added to the ethanol processing fluid at temperatures of about 20° C. to about 80° C., for example, about 20° C. to about 77° C., about 40° C. to about 65° C., or about 30° C. to about 55° C. (e.g., 52° C.). In an aspect, the phytase is added to the ethanol processing fluid at temperatures sufficient to allow the reaction between phytate and phytase to proceed to completion without degrading the enzyme. In another aspect, the phytase is added to the ethanol processing fluid at pH of about 3 to about 9, for example, about 4.0 to about 5.0, about 4.0 to about 5.5, or about 4.0 to about 5.3. In yet another aspect, the phytase is added at a pH of 4.0, and the reaction is conducted at temperatures of about 40° C. to about 65° C., about 20° C. to about 77° C., or about 30° C. to about 55° C. (e.g., 52° C.).

In an aspect, the phytase is added to the ethanol processing fluids at a concentration of about 100 ppm to about 500 ppm. In another aspect, the phytase is added at a concentration of 100 ppm, and in yet another aspect, the phytase is added at a concentration of 500 ppm. The phytase can be added at concentrations expressed in phytase units. A unit of activity (U) is the amount of phytase that can release 1 μmol of ortho-phosphate per minute from excess phytic acid/phytate, at a temperature of 37° C. and a pH of about 5.5. Therefore, in an aspect, the phytase is added at a concentration of about 500 U/L to about 2500 U/L. In another aspect, the phytase is added at a concentration of 100 U/L, and in yet another aspect, the phytase is added at a concentration of 2500 U/L.

In an embodiment, the phytase is added to ethanol processing fluids at lower concentrations, and the reaction is allowed to proceed over longer periods of time. Extending the reaction time or residence time allows smaller amounts of enzymes to be used, making ethanol processing more economical. In an aspect, the phytase is added to the ethanol processing fluids for a residence time sufficient for complete reaction of the phytase with the insoluble phytate. In another aspect, the phytase is added for a residence time of about 2 minutes to about 1200 minutes, for example, about 3 minutes to about 200 minutes, or about 3 minutes to about 40 minutes.

As shown in Table 3, low concentrations of phytase can release significant amounts of ortho-phosphate, if reacted over longer periods of time. For example, 5 ppm of phytase will release approximately 900 ppm of ortho-phosphate when reacted over a 20 hour time period. In contrast, 100 ppm of phytase releases 400-500 ppm of ortho-phosphate in just 10 minutes.

TABLE 3

Orthophosphate Formation at Low Doses of Phytase

| Time (min) | Amount of Released Ortho-Phosphate (ppm) | | |
|---|---|---|---|
| | 5 ppm phytase | 10 ppm phytase | 20 ppm phytase |
| 20 | 73 | 92 | 109 |
| 60 | 143 | 232 | 387 |
| 140 | 260 | 436 | 732 |
| 260 | 377 | 636 | 933 |
| 1200 | 894 | 1460 | 1713 |

Therefore, in an aspect, the phytase is added at a concentration of about 5 ppm to about 20 ppm. In another aspect, the phytase is added at a concentration of 5 ppm. In a further aspect, the phytase is added at a concentration of 10 ppm, and in a yet further aspect, the phytase is added at a concentration of 20 ppm. These concentrations may also be expressed in phytase units such that, in an aspect, the phytase is added at a concentration of about 25 U/L to about 100 UI. In another aspect, the phytase is added at a concentration of 25 U/L. In a further aspect, the phytase is added at a concentration of 50 U/L and in a yet further aspect, the phytase is added at a concentration of 100 U/L.

In an embodiment, the present invention provides a method in which the agent added to the ethanol processing fluid converts soluble phytate, phytate suspension, phytate precipitate, or phytate scale into soluble orthophosphate. In an aspect, the agent is an enzyme such as phytase, which specifically hydrolyzes phytate. The enzyme can be used to convert phytate materials into soluble phosphates that are easily removed from the processing fluid, if necessary. Assuming identical conditions of pH (5.3) and identical concentrations of $Mg^{2+}$ ions (1048 ppm) and phytic acid (4702 ppm), samples of processing fluid treated with phytase remained clear (i.e., phosphates remain in solution without precipitating out). However, samples of processing fluid not exposed to phytase showed progressively more precipitation of magnesium phytate as the temperature is increased, as shown in Table 3 below.

TABLE 4

Enzyme Treatment Prevents Precipitation

| Enzyme Treated? (Y/N) | Temp (° C.) | Precipitate? (+/−) |
|---|---|---|
| Y | 20 | − |
| Y | 40 | − |
| Y | 80 | − |
| Y | 100 | − |
| N | 20 | + |
| N | 40 | ++ |
| N | 60 | + |
| N | 80 | +++ |

The following examples are provided to illustrate various aspects of the invention, and should not be construed to limit the invention. A person of skill in the art will recognize that various modifications may be made to the examples without departing from the scope of the present invention.

EXAMPLES

Example 1

Conventional Analyses Indicate that Deposits in the Beer Column Contain Phosphorus, But Do Not Reveal That the Phosphorus is in Phytate The content of various solid deposits formed during ethanol fermentation can be determined using standard methods. It was previously thought that the solid deposits in the beer column were primarily beerstone (i.e. calcium oxalate). The unexpected results shown in the following examples demonstrate, however, that a large percentage of the solid deposits found in the beer column are in the form of phosphates, i.e. $P_2O_5$.

Materials and Methods

To determine the content of the solid deposit in the beer column, X-ray fluorescence (XRF) analysis was used. A sample of solid deposit from the beer column was collected and air-dried. A portion of the sample was ground to approximately 400 mesh using a steel swing mill, and the ground sample was analyzed by XRF. Using standard XRF procedures, it was possible to determine the presence of 31 major, minor and trace elements to a relative precision/accuracy of approximately 5-10% for major and minor elements and approximately 10-15% for trace elements. A replicate sample was analyzed, along with a standard reference material ("SY3", a CANMET standard rock or geological sample) to demonstrate analytical reproducibility as well as analytical accuracy for a geological standard.

Results

The content of the solid deposit in the beer column was as shown in Table 5. Major elements in the solid deposit include magnesium (as MgO) and phosphorus (as $P_2O_5$), while potassium and calcium (as their respective oxides $K_2O$ and CaO) occur as minor elements. Trace amounts of zinc were also detected. Major and minor elements were represented as weight percentages of the deposit, while trace elements were represented in ppm units.

TABLE 5

Deposit Analysis

| Element | Content |
| --- | --- |
| Magnesium (as MgO) | 12.5 wt % |
| Phosphorus (as $P_2O_5$) | 35.7 wt % |
| Potassium (as $K_2O$) | 2.54 wt % |
| Calcium (as CaO) | 2.76 |
| Zinc | 18447 ppm |

Conclusions

The results in Table 5 demonstrate that the majority of the solid deposits are present as phosphate (rather than as the expected beerstone or calcium oxalate). XRF analysis of solid deposits shows a large concentration of magnesium and phosphorus present in the oxide form, but does not distinguish between different chemical forms of phosphorus or phosphate salts, and does not specify if some of the magnesium was actually present as a phosphate salt (i.e. magnesium phytate). Because different forms of phosphorus and phosphate salts have different solubilities and because the phytase has different activities on different forms of phosphate, it is useful to distinguish between the various forms.

Example 2

The Deposits Include Substantial Amounts Phosphorus in Phytate

Because the activity of the phytase on the solid deposits is dependent on the type of phosphorus or phosphate salts present, wet analysis of various deposit samples was used to determine the different forms of phosphorus and phosphate salts present in the solid deposits of the beer column.

Materials and Methods

Deposit samples from ethanol plants were dissolved in a weighed amount of acid, the acid was neutralized and the solution was diluted to a known volume. A portion of the neutralized sample was then subjected to a standard test for ortho-phosphate ($PO_4^{3-}$), i.e. the Hach test. Total phosphorus was determined by acid oxidation with persulfate, followed by the reactive phosphorus test. Organically bound ortho phosphate was then determined by subtracting the acid-hydrolysable phosphorus content, and was reported as $PO_4^{3-}$ or ortho-phosphate.

A separate portion of the neutralized solution was treated with phytase (at a concentration of 500 ppm and 41° C. for 20-30 minutes). Under these conditions, phytate present in the solution was converted to ortho-phosphate. The amount of ortho-phosphate ($PO_4^{3-}$) present after phytase treatment represents the total phosphorus content of the deposit (total P as $PO_4^{3-}$), i.e. original ortho phosphate and phytate phosphorus.

Results

As indicated in Table 6, deposit samples from an evaporator at one plant, and samples from cook water lines and liquefaction pumps at a second plant had between 60% and 75% of their phosphorus content as phytate, confirming that the deposit in the beer column included primarily magnesium phytate.

TABLE 6

Comparison of Deposit Analysis by XRF and Wet Methods

| | Content by XRF | | Content by Wet Analysis | |
| --- | --- | --- | --- | --- |
| | | | | Total % P |
| Sample | % MgO | % $P_2O_5$ | % $PO_4^{3-}$ | as $PO_4^{3-}$ |
| Plant 1 Evaporator (1) | 14.6 | 36.8 | 7.4 | 37.4 |
| Plant 1 Evaporator (2) | 11.3 | 23.0 | 1.9 | 27.7 |
| Plant 1 Evaporator (3) | 10.5 | 25.5 | 5.9 | 30.9 |
| Plant 2 Cook Water | 14.0 | 35.5 | 2.4 | 36.0 |
| Plant 2 Pump | 16.7 | 35.2 | 9.1 | 38.0 |

Conclusions

The results in Table 6 demonstrate that the solid deposits were present as phytate salt, i.e. magnesium phytate. This is an important discovery because the activity of the phytase added to various structures in an ethanol plant depends on the presence of phosphate primarily in the phytate form. Solid deposits that exist primarily as phytate can be dissolved by the action of the phytase.

Example 3

Phytase Reduces the Phytate Concentration in Thin Stillage, Which is the Source of the Deposits Materials and Methods The amount of phosphorus (present as ortho phosphate) in the thin stillage fraction collected from an ethanol plant will decrease once phytase has been added. To determine the decrease in ortho-phosphate concentration over time as a result of enzyme activity, thin stillage fractions were collected and treated with phytase at temperatures from 43° C. to 62° C., at a pH of 4.0. The phytase concentration was either 100 ppm or 500 ppm. After adding the enzyme, ortho-phosphate concentration was measured at various time points (e.g., from 3 minutes to 20 minutes). Any phosphorus present as phytate (about 40-50% of the total phosphate) was converted to ortho phosphate ($PO_4^{3-}$) by the action of the phytase, with more phytate converted over increasing periods of time. The concentration of ortho-phosphate in the thin stillage was therefore a measure of enzyme activity.

Results As demonstrated in Table 7, at an enzyme concentration of 500 ppm and a temperature of 43° C., the reaction was essentially complete in 5 minutes, indicating that phytate was completely converted to ortho phosphate. At an enzyme concentration of 100 ppm, and a temperature of 62° C., the reaction continued for 20 minutes.

TABLE 7

Conversion of Phytate in Thin Stillage to Ortho Phosphate

| Sample/Run (min) | Enzyme Conc. (ppm) | Temp (° C.) | Phosphate Conc. (ppm) | Released $PO_4^{3-}$ Conc. (ppm) |
|---|---|---|---|---|
| Distilled Water (zero) | — | — | 0 | — |
| Std. 1 - 640 ppm $PO_4^{3-}$ | — | — | 732 | — |
| Std. 2 - 1280 ppm $PO_4^{3-}$ | — | — | 1234 | — |
| Run 1 | | | | |
| 5 min | 500 | 45.5 | 3313 | 1463 |
| 10 min | 500 | 43.3 | 3385 | 1536 |
| Std 2 | | | 1242 | — |
| Run 2 | | | | |
| 3 min | 100 | 63.3 | 1688 | 137 |
| 5 min | 100 | 62.8 | 2146 | 595 |
| 10 min | 100 | 62.2 | 2214 | 663 |
| 20 min | 100 | 61.0 | 2859 | 1309 |

Conclusions

The results shown in Table 7 indicate that substantially all of the phosphorus present in the phytate form was converted and released as ortho-phosphate by the action of the phytase. About half of the total phosphorus content of the thin stillage was in the form of phytate, and complete reaction of the enzyme with the phosphorus resulted in the conversion of phytate and release of ortho-phosphate. The amount or concentration of released ortho-phosphate therefore provides a measure of the activity of the phytase.

Example 4

Increased Solubility on Conversion of Phytate to Ortho-phosphate

The solid deposits formed in various structures in an ethanol plant include primarily insoluble magnesium phosphate salts, including magnesium phytate. The following example illustrates that the solubility of these salts is unexpectedly increased in the presence of phytase.

Materials and Methods

To determine the effect of phytase on increasing the solubility of magnesium phytate, two solutions of magnesium phytate were prepared by mixing magnesium salt with phytic acid in two separate test tubes. The solution in one test tube was treated with phytase, while the other was left untreated. The two solutions were maintained at the same temperature and pH and had identical magnesium and total phosphorus content.

Results

The action of the phytase on magnesium phytate converted the insoluble phytate salt into soluble ortho phosphate, which can then be readily removed from pumps, lines and evaporators in an ethanol plant.

The enzyme-treated solution in one test tube remained clear, indicating that all the phytate was converted to soluble ortho phosphate. The untreated solution showed precipitate formation, indicating the presence of insoluble magnesium phytate. This demonstrated that the enzyme completely converted the phytate to ortho-phosphate and greatly increased the solubility of the magnesium salt.

Conclusion

Phytase can prevent solid deposits of magnesium phosphate salts from forming in various structures in an ethanol plant.

Unless defined otherwise, all technical and scientific terms used herein have the same meaning as commonly understood by one of ordinary skill in the art. Although any methods, devices and material similar or equivalent to those described herein can be used in practice or testing, the methods, devices and materials are now described.

All publications and patent applications in this specification are indicative of the level of ordinary skill in the art to which this invention pertains and are incorporated herein by reference in their entireties.

In this specification and the appended claims, the singular forms "a," "an," and "the" include plural reference, unless the context clearly dictates otherwise. Unless defined otherwise, all technical and scientific terms used herein have the same meaning as commonly understood to one of ordinary skill in the art.

The various embodiments described above are provided by way of illustration only and should not be construed to limit the invention. Those skilled in the art will readily recognize various modifications and changes that may be made to the present invention without following the example embodiments and applications illustrated and described herein, and without departing from the true spirit and scope of the present invention without following the example embodiments and applications illustrated and described herein, and without departing from the true spirit and scope of the present invention, which is set forth in the following claims.

The claimed invention is:

1. A method of reducing the formation of insoluble deposits of phytic acid or phytic (phytate) acid salts in a fermentation equipment, the method comprising:
    identifying the insoluble deposits forming material as phytic acid or phytic acid (phytate) salts;
    adding an agent to fermentation fluids prior to fermentation; and
    removing soluble residues from the fermentation equipment, thereby reducing the formation of insoluble deposits of phytic acid or phytic acid (phytate) salts in the fermentation equipment.

2. The method of claim 1, wherein the deposit forming materials is identified using x-ray fluorescence and elemental analysis.

3. The method of claim 1, wherein the deposit forming material is identified using oxidation and elemental analysis.

4. The method of claim 1, wherein the deposit forming material contains phosphate salt.

5. The method of claim 1, wherein the deposit forming material contains phytate salt.

6. The method of claim 1, wherein the deposit forming material contains magnesium phytate.

7. The method of claim 1, wherein the agent used is an acidic compound in the presence of a strong oxidizer or oxidizing agent.

8. The method of claim 1, wherein the agent used is an acidic compound in the presence of ultraviolet light.

9. The method of claim 1, wherein the agent used is an enzyme with phytase activity.

10. The method of claim 9, wherein the enzyme is phytase.

11. The method of claim 10, wherein adding comprises introducing the agent into the processing fluid at a temperature from about 20° C. to about 80° C.

12. The method of claim 10, wherein adding comprises introducing the agent into the processing fluid at a pH of about 3.0 to 9.0.

13. The method of claim 10, wherein adding comprises introducing the agent for a residence time sufficient for complete reaction of the agent with insoluble deposits of phytic acid or salts of phytic acid.

14. The method of claim 10, wherein adding comprises introducing the agent into the processing fluid at a concentration of about 5 ppm to about 20 ppm.

15. The method of claim 10, wherein adding comprises introducing the agent into the processing fluid at a concentration of about 100 ppm to about 500 ppm.

16. The method of claim 10, wherein adding comprises introducing the agent into the processing fluid at a concentration of about 25 U/L to about 100 U/L.

17. The method of claim 10, wherein adding comprises introducing agent for a residence time from about 2 minutes to about 1200 minutes.

\* \* \* \* \*